United States Patent [19]

Vallejos et al.

[11] Patent Number: 5,395,964

[45] Date of Patent: Mar. 7, 1995

[54] PREPARATION PROCESS FOR HYDROXYPHENYLACETIC ACIDS

[75] Inventors: Jean-Claude Vallejos; Yani Christidis, both of Paris, France

[73] Assignee: Societe Francaise Hoechst, Puteaux, France

[21] Appl. No.: 245,898

[22] Filed: May 19, 1994

[30] Foreign Application Priority Data

May 28, 1993 [FR] France .................. 93 06433

[51] Int. Cl.$^6$ .................................................. C07C 65/01
[52] U.S. Cl. .................................. 562/478; 562/465
[58] Field of Search .................................. 562/478

[56] References Cited

U.S. PATENT DOCUMENTS 5,145,994 9/1992 Mandal et al. ...................... 562/478

FOREIGN PATENT DOCUMENTS

| | | |
|---|---|---|
| 0028375 | 5/1981 | European Pat. Off. . |
| 0032374 | 7/1981 | European Pat. Off. . |
| 0224401 | 6/1987 | European Pat. Off. . |
| 0526672 | 2/1992 | European Pat. Off. . |
| 0536960 | 4/1993 | European Pat. Off. . |
| 0554636 | 8/1993 | European Pat. Off. . |

(List continued on next page.)

OTHER PUBLICATIONS

Rosenmund et al., *Hydroxycarboxylic Acids,* $C_8H_8O_3$-2-Hydroxyphenylacetic acid, $C_8H_8O_3$, Arch. Pharm., vol. 1928, p. 282.
Robinson et al., *Hydroxycarboxlyic Acids,*

(List continued on next page.)

*Primary Examiner*—Paul J. Killos
*Attorney, Agent, or Firm*—Browdy and Neimark

[57] ABSTRACT

Preparation process for a hydroxyphenylacetic acid of formula (I):

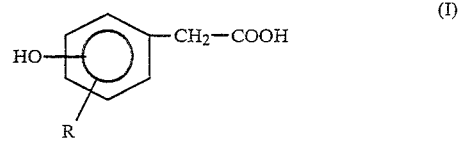

where R=H, alkyl or alkoxyl as well as its salts, in which the corresponding free or salified hydroxymandelic acid of formula (II):

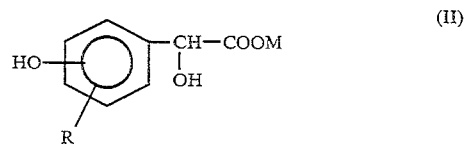

in which R has the meaning given previously and M=H, K or an ammonium group is reacted in an aqueous medium, at a temperature greater than or equal to 50° C., with formic acid in the presence of catalytic quantities of an oxygenated derivative of sulphur having a degree of oxidation from 2 to 4, in order to obtain the hydroxyphenylacetic acid of formula (I) which is isolated or, if desired, is salified according to the usual methods and the hydroxyphenylacetic acid thus obtained.

19 Claims, No Drawings

FOREIGN PATENT DOCUMENTS

| | | |
|---|---|---|
| 2426669 | 12/1979 | France . |
| 2427322 | 12/1979 | France . |
| 2440350 | 5/1980 | France . |
| 2445311 | 7/1980 | France . |
| 2495137 | 6/1982 | France . |
| 2588869 | 4/1987 | France . |
| 2638740 | 5/1990 | France . |
| 170960 | 6/1992 | India . |
| 55-92344 | 7/1980 | Japan . |
| 58-52242 | 3/1983 | Japan . |
| 2078718 | 1/1982 | United Kingdom . |

OTHER PUBLICATIONS $C_8H_8O_3$–3–*Hydroxyphenylacetic acid*, $C_8H_8O_3$, J. Chem. Soc., vol. 1927, p. 2412.

Baeyer et al., *Hydroxycarboxylic Acids*, $C_8H_8O_3$–2–*Hydroxyphenylacetic acid, 2-hydroxy-α-toluic acid*, $C_8H_8O_3$, Ber., vol. 17, p. 974; Fritsch, doctoral dissertation (Munich, 1888), p. 16.

Offe et al., *Hydroxycarboxylic Acids*, $C_8H_8O_3$–(2-Hydroxyphenyl)acetic acid, BER., vol. 80, pp. 469 & 472, 1947.

Kornfeld, (3–*Hydroxyphenyl*)*acetic acid*, J. Am. Chem. Soc., vol. 70, p. 1373 & 1375, 1948; cf. E II, 112.

Späth et al., (4–*Hydroxyphenyl*)*acetic acid*, BER., vol. 74, pp. 189 & 191, 1941.

Ghose et al., (2–*Hydroxyphenyl*)*acetic acid*, $C_8H_8O_3$, Sci. Culture, vol. 20, p. 95, 1954.

Shaw et al., (3–*Hydroxyphenyl*)*acetic acid*, $C_8H_8O_3$, J. Org. Chem., vol. 1149, 1956.

Kraetzl et al., (4–*Hydroxyphenyl*)*acetic acid*, $C_8H_8O_3$, Monatsh., vol. 83, pp. 1045 & 1050, 1952.

McKenzie et al., *Hydroxy-(2-hydroxyphenyl)acetic acid, 2–hydroxymandelic acid*; $C_8H_8O_4$, J. Chem. Soc., vol. 1935, pp. 104 & 111.

Hahn et al., 3–*Hydroxy-DL-mandelic acid nitrile*, 3-hydroxy–DL–mandelonitrile, $C_8H_7NO_2$, BER., vol. 71, pp. 2154, 2158, & 2162, (1938), Cf. E 11, 270.

Pratesi et al., *Hydroxyphenyl–(4–hydroxyphenyl)acetic acid, 4-hydroxymandelic acid*, $C_8H_8O_4$, Farmaco, Ed. Scient., vol. 10, pp. 563 & 569, 1955.

Shaw et al., 3–*Hydroxy–DL–mandelic acid*, $C_8H_8O_4$, *formula II* ($R=R'=X=H$), J. Org. Chem. vol. 21, p. 1149, 1956.

Shaw et al., 3–*Hydroxy-DL–mandelonitrile*, $C_8H_7NO_2$, J. Org. Chem., vol. 21, p. 1149, 1956.

PREPARATION PROCESS FOR HYDROXYPHENYLACETIC ACIDS

The present application relates to a preparation process for hydroxyphenylacetic acids.

The o-, m- and p-hydroxyphenylacetic acids substituted or not substituted on the aromatic nucleus by one or more substituents chosen from halogens or alkyl or alkoxyl radicals are raw materials currently used in organic synthesis for accessing products which have useful physiological properties.

A large number of processes for obtaining these hydroxyphenylacetic acids are known. Among these there can be mentioned hydrogenolysis either by catalytic route, or by chemical route, of the corresponding hydroxymandelic acids which may have originated from the hydrolysis of the corresponding hydroxymandelonitrile, or for some of them, from the condensation of glyoxylic acid with the corresponding phenol (cf Beil., 10, 410, 10, I, 199, 10-III, 1471 and 1474, 10-V, 1518, EP-A-536 960, FR-A-2 440 350, 2 427 322, 2 495 137, 2 638 740). The known processes for the hydrogenolysis of hydroxymandelic acids into the corresponding hydroxyphenylacetic acids, however, present serious disadvantages on an industrial level due in particular to the high price of some of the reactive agents used, such as hydroiodic acid, iodine, red phosphorus, phosphorous acid or tin or chromium salts (FR -A-2 426 669, 2 445 311, 2 588 869, GB-A-2 078 718, U.S. Pat. No. 5,145,994, EP-A-028 375, 032 374, 526 672 and 224 401, JP-A- 50/092 344, 58-052 242, Beil. 10, 187, 189, 190, 10, I, 81, 82, 10, II, 112, 10, III, 422, 428, 430, 10, IV, 536, 541, 543).

In order to overcome these disadvantages, the Applicant has discovered with astonishment a new process for the preparation of hydroxyphenylacetic acids.

A subject of the present invention is a preparation process for a hydroxyphenylacetic acid of formula (I):

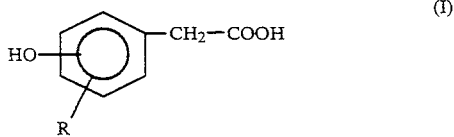

(I)

in which R represents a hydrogen atom, a halogen atom or an alkyl or alkoxyl group.

The term alkyl can designate, for example, a $C_1$–$C_5$ radical, such as a methyl, ethyl, n-propyl, isopropyl, n-butyl, isobutyl, sec-butyl, tertiobutyl, pentyl radical.

The term alkoxyl can designate, for example, a $C_1$–$C_5$ radical such as a methoxyl, ethoxyl, propoxyl, isopropoxyl, butoxyl, isobutoxyl, sec-butoxyl, tertiobutoxyl, pentyloxyl radical.

The term halogen designates chlorine or bromine.

According to the invention, the preparation process for hydroxyphenylacetic acids of formula (I) and their salts is characterized in that the corresponding free or salified hydroxymandelic acid of formula (II):

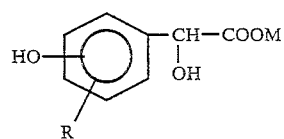

(II)

in which R has the meaning given previously and M represents a hydrogen, sodium, potassium atom or an ammonium group is reacted in an aqueous medium, at a temperature greater than or equal to 50° C., with formic acid in the presence of catalytic quantities of an oxygenated derivative of sulphur having a degree of oxidation from 2 to 4, in order to obtain the hydroxyphenylacetic acid of formula (I) which is isolated or, if desired, is salified according to the usual methods.

Among the oxygenated derivatives of sulphur having a degree of oxidation from 2 to 4, the following can be mentioned: sodium or potassium hydrogen sulphite, sodium or potassium sulphite, sodium or potassium disulphite, sodium or potassium thiosulphate, sodium or potassium dithionite, sodium formaldehyde sulphoxylate, sulphur dioxide.

Under the preferred conditions for the implementation of the invention, the process described above is carried out in the following way:
- at a temperature comprised between 75° and 150° C.,
- at a pressure of 2 to 10 bars,
- in the presence of catalytic quantities of sodium disulphite.

Under more particularly preferred conditions, the process described above is implemented in the following way:
- at a temperature comprised between 100° to 130° C. and
- at a pressure of 4 to 5 bars.

Under other even more preferred conditions, the process described above is implemented in the following way:
- from the corresponding hydroxymandelic acid (II with M equal to H),
- in the presence of 0.10±0.02 mole of sodium disuphite per mole of corresponding hydroxymandelic acid used at the start,
- in the presence of 1.1±0.1 mole of formic acid per mole of corresponding hydroxymandelic acid used at the start.

The hydroxymandelic acid, II with M=H, can be prepared extemporaneously in the reaction medium from one of the alkali metal or ammonium salts by the action of a stoichiometric quantity of a mineral or organic acid such as hydrochloric acid, sulphuric acid, orthophosphoric acid.

Among the hydroxyphenylacetic acids of formula (I), the following can be mentioned in particular:
- orthohydroxyphenylacetic acid,
- parahydroxyphenylacetic acid,
- 4-hydroxy 3-methoxy phenylacetic acid,
- 4-chloro 2-hydroxy phenylacetic acid.

At the end of the reaction, the hydroxyphenylacetic acid of formula (I) is isolated from the reaction medium by means which are known per se. Among the latter, one of the simplest means consists of concentrating the reaction medium, acidifying to a pH less than or equal to 2 with a mineral acid under reduced pressure until crystallization of the desired acid which is then isolated by filtration.

The desired acid can also be extracted with a suitable solvent which is insoluble in water such as ethyl acetate, diethyl oxide.

The starting products of formula (II) are either known products or products which are easily accessible via known processes such as the condensation of sodium cyanide with the corresponding hydroxybenzaldehyde followed by hydrolysis of the hydroxymandelonitrile obtained.

The following examples illustrate the present invention without however limiting it.

EXAMPLE 1

104 g (0.5 mole) of pure sodium parahydroxymandelate crystallized with one molecule of water is dissolved in 400 g of water, then the following is introduced under agitation:
- 57.6 g (0.5 mole) of orthophosphoric acid in 85% aqueous solution, then the following are introduced under agitation into the solution obtained:
- 7.6 g (40 mmoles) of pure sodium metabisulphite (sodium disulphite), then,
- 25.3 g (0.55 mole) of 98–100% formic acid.

This solution is then heated in an autoclave under agitation for 9 hours at 120° C. under a pressure of 5 bars.

The reaction medium is then cooled down to ambient temperature and then taken to atmospheric pressure. In the solution obtained 74.5 g of parahydroxyphenylacetic acid, designated hereafter APHPA, is determined by high performance liquid chromatography, HPLC, i.e. a yield of 98% of the calculated theoretical value relative to the sodium parahydroxymandelate used.

The reaction medium is acidified to pH=2 with 15 g (0.13 mole) of orthophosphoric acid in 85% aqueous solution, then 200 g of water is eliminated by distillation under reduced pressure. By cooling down the reaction medium to ambient temperature, the expected parahydroxyphenylacetic acid crystallizes spontaneously. A first batch of 55.3 g (0.3635 mole) of pure crystallized parahydroxyphenylacetic acid is obtained having a melting point of 150° C. By concentrating the mother liquors, a second batch of 13.5 g (0.09 mole) is isolated, which after recrystallization from water produces pure APHPA.

EXAMPLE 2

A solution constituted by:
- 104 g (0.5 mole) of pure sodium parahydroxymandelate crystallized with one molecule of water,
- 400 g of water,
- 25.3 g (0.55 mole) of pure formic acid,
- 7.6 g (40 mmoles) of pure sodium metabisulphite, is heated under agitation in an autoclave for 12 hours at 100° C. under a pressure of 2 bars.

At the end of the reaction, 46.4 g of APHPA is determined in the reaction solution by HPLC, i.e. a yield of 61% of the calculated theoretical value relative to the sodium parahydroxymandelate used.

EXAMPLE 3

The operation is carried out as in Example 2, but heating only takes place for 9 hours at 100° C. under a pressure of 5 bars. At the end of the reaction 45.6 g of APHPA is determined in the reaction solution (yield 60%).

EXAMPLE 4

The operation is carried out as in Example 1, but heating only takes place for 9 hours at 100° C. under a pressure of 5 bars. At the end of the reaction 69.2 g of APHPA is determined in the reaction solution (yield 91%).

EXAMPLE 5

The following are heated for 8 hours at 100° C., in an autoclave, under agitation and under a pressure of 5 bars:
- 104 g (0.5 mole) of sodium parahydroxymandelate crystallized with one molecule of water,
- 23 g (0.5 mole) of pure formic acid,
- 57.6 g (0.5 mole) of orthophosphoric acid at 85% in water,
- 10.4 g (0.06 mole) of pure sodium dithionite,
- 400 g of water.

At the end of the reaction 0.425 mole of parahydroxyphenylacetic acid is determined in the reaction solution (yield 85%).

We claim:

1. Preparation process for a hydroxyphenylacetic acid of formula (I):

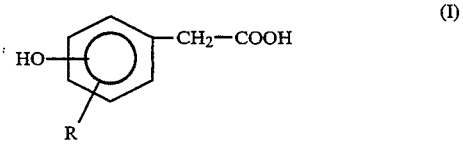

in which R represents a hydrogen atom, a halogen atom or an alkyl or alkoxyl group as well as its salts, characterized in that the corresponding free or salified hydroxymandelic acid of formula (II):

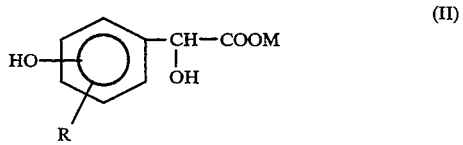

in which R has the meaning given previously and M represents a hydrogen, sodium, potassium atom or an ammonium group, is reacted in an aqueous medium, at a temperature greater than or equal to 50° C., with formic acid in the presence of catalytic quantities of an oxygenated derivative of sulphur having a degree of oxidation from 2 to 4, in order to obtain the hydroxyphenylacetic acid of formula (I) which is isolated or, optionally, is salified.

2. Process according to claim 1, characterized in that the oxygenated derivative of sulphur having a degree of oxidation from 2 to 4, is chosen from the group constituted by sulphur dioxide, sodium or potassium hydrogen sulphite, sodium or potassium sulphite, sodium or potassium disulphite, sodium or potassium dithionite, sodium or potassium thiosulphate.

3. Process according to claim 1, characterized in that it is carried out at a temperature comprised between 75° and 150° C.

4. Process according to claim 1, characterized in that it is carried out under a pressure of 2 to 10 bars.

5. Process according to claim 1, characterized in that the starting product of formula (II) is hydroxymandelic acid of formula (II) in which M represents a hydrogen atom.

6. Process according to claim 1, characterized in that it is carried out in the presence of 1.1±0.1 mole of formic acid per mole of starting product.

7. Process according to claim 1, characterized in that it is carried out under a pressure of 4 to 5 bars and at a temperature of 100° to 130° C.

8. Process according to claim 1, characterized in that it is carried out in the presence of catalytic quantities of sodium disulphite.

9. Process according to claim 1, characterized in that it is carried out in the presence of 0.10±0.02 mole of sodium disulphite per mole of starting product.

10. Process according to claim 2, characterized in that it is carried out at a temperature comprised between 76° and 150° C.

11. Process according to claim 10 characterized in that it is carried out under a pressure of 2 to 10 bars.

12. Process according to claim 11, characterized in that the starting product of formula (II) is hydroxymandelic acid of formula (II) in which M represents a hydrogen atom.

13. Process according to claim 4, characterized in that the starting product of formula (II) is hydroxymandelic acid of formula (II) in which M represents a hydrogen atom.

14. Process according to claim 13, characterized in that it is carried out in the presence of 1.1±0.1 mole of formic acid per mole of starting product.

15. Process according to claim 14, characterized in that it is carried out under a pressure of 4 to 5 bars and at a temperature of 100° to 130° C.

16. Process according to claim 15, characterized in that it is carried out in the presence of catalytic quantities of sodium disulphite per mole of starting product.

17. Process according to claim 16, characterized in that it is carried out in the presence of 0.10±0.02 mole of sodium disulphite per mole of starting product.

18. Process according to claim 8, characterized in that it is carried out in the presence of 0.10±0.02 mole of sodium disulphite per mole of starting product.

19. Process according to claim 3, characterized in that the starting product of formula (II) is hydroxymandelic acid of formula (II) in which M represents a hydrogen atom.

* * * * *